United States Patent [19]
Gaglani

[11] Patent Number: 5,906,981
[45] Date of Patent: May 25, 1999

[54] HALOPROPARGYL INCLUSION COMPLEXES

[75] Inventor: Kamlesh D. Gaglani, Belle Mead, N.J.

[73] Assignee: Troy Corporation, Florham Park, N.J.

[21] Appl. No.: 08/655,091

[22] Filed: Jun. 4, 1996

[51] Int. Cl.⁶ .......................... A61K 31/715; A61K 31/27
[52] U.S. Cl. ............................. 514/58; 514/478; 536/103
[58] Field of Search ....................... 514/58, 478; 536/103

[56] References Cited

U.S. PATENT DOCUMENTS

| | | | |
|---|---|---|---|
| 3,923,870 | 12/1975 | Singer | 260/482 C |
| 4,259,350 | 3/1981 | Morisawa et al. | 424/308 |
| 4,418,144 | 11/1983 | Okada et al. | 435/96 |
| 4,552,885 | 11/1985 | Gabriele et al. | 514/316 |
| 4,592,773 | 6/1986 | Tanaka et al. | 71/88 |
| 4,616,004 | 10/1986 | Edwards | 514/63 |
| 4,719,227 | 1/1988 | Schade et al. | 514/452 |
| 4,920,214 | 4/1990 | Friedman et al. | 536/103 |
| 4,945,109 | 7/1990 | Raydu | 514/478 |
| 5,024,998 | 6/1991 | Bodor | 514/58 |
| 5,134,127 | 7/1992 | Stella et al. | 514/58 |
| 5,324,718 | 6/1994 | Loftsson | 514/58 |
| 5,376,641 | 12/1994 | Ammeraal | 514/26 |
| 5,376,645 | 12/1994 | Stella et al. | 514/58 |
| 5,426,184 | 6/1995 | Pitha et al. | 536/17.2 |
| 5,455,236 | 10/1995 | Muller et al. | 514/58 |

FOREIGN PATENT DOCUMENTS 5-117105   5/1993   Japan .

OTHER PUBLICATIONS

"Synthesis of Chemically Modified Cyclodextrins," Croft, A.P., et al., *Tetrahedron,* 39 (9): 1417–1474 (1983).

"Medicinal Applications of Cyclodextrins," Szejtli, J., *Medicinal Research Reviews,* 14 (3): 353–386 (1984).

*Primary Examiner*—Howard C. Lee
*Attorney, Agent, or Firm*—Banner & Witcoff, Ltd.

[57] ABSTRACT

A biocidal composition which comprises an inclusion complex of a halopropargyl compound and a cyclodextrin or a modified cyclodextrin, useful broadly in industrial systems and more particularly in aqueous compositions used in connection with paints, coatings, stucco, concrete, stone, cementaceous surfaces, wood, caulking, sealants, textiles, and the like.

21 Claims, 2 Drawing Sheets

THE STRUCTURES OF ALPHA, BETA GAMMA CYCLODEXTRINS.

HALOPROPARGYL INCLUSION COMPLEXES

BACKGROUND OF THE INVENTION

1. Field of the Invention

This invention is directed to biocidal compositions containing a haloalkynyl compound, and especially a halopropargyl compound. The invention is specifically directed to compositions containing inclusion complexes of such halopropargyl compounds. In its preferred form, the present invention is directed to water soluble inclusion complexes of such halopropargyl compounds, especially those made water soluble by the use of a modified cyclodextrin.

2. Description of Related Art

Both exterior and interior surfaces and substrates of all types, when exposed to common environmental conditions, e.g., moisture, are prone to attack, discoloration and various kinds of destruction by a variety of species of microorganisms, including fungi, algae, bacteria and protozoa. The end result of such microbial attack is decomposition of the material, unsightly defacement or foul odors. In this respect microorganisms are a formidable enemy. They are basically found everywhere on the earth, in the water and in the air. They survive under diverse conditions such as in dust, nearly boiling water in hot springs and in salty water with a salt concentration of up to 30%, in light or darkness, and with small or large amounts of moisture and a wide range of nutrients. As a result, there is a great need and requirement for an effective and economical means to protect, for extended periods of time, both exterior and interior surfaces and various types of substrates and commercial formulations from the deterioration and destruction caused by such microorganisms.

Materials which need protection with a suitable antimicrobial composition include stucco, concrete, stone, cementaceous surfaces, iron, wood, caulking, sealants, leather, rope, paper pulp, plastics, textiles, biodegradable compositions including such materials as paints and other coating formulations, surfactants, proteins, starch-based compositions, stabilizers, inks, emulsifying agents, cellulose products, emulsions or suspensions, resins, shampoos, creams, lotions, cosmetics, soaps, and household products such as laundry detergents, hard surface cleaners, and fabric softeners, as well as numerous other materials and other substances which may be attacked by destructive microbes. Many of these applications would greatly benefit from an aqueous biocidal composition or they require a biocidal composition containing a large amount of water. For example, some of the above applications such as ink, sap stain, leather, textiles, surfactants, thickeners, metal working fluids, paper pulp, cellulose products, shampoos, creams, lotions, soaps, thickeners etc. consist of a large amount of water. For such applications, it is desirable to have a biocide which is water soluble for ease of incorporation, physical stability of the formulation and perhaps enhanced efficacy.

A wide variety of materials have been identified which, to various degrees, are effective in retarding or preventing the growth of, and accompanying destruction caused by such microbes. Such biocidal compounds include halogenated compounds, organometallic compounds, quaternary ammonium compounds, phenolics, metallic salts, heterocyclic amines, formaldehyde donors, organo-sulfur compounds and the like.

Formulated products that are protected against microbial attack by the inclusion of such biocidal additives must retain their biocidal activity for a prolonged time period to be most useful. Indeed, such products often are used to impart a biocidal activity to another product or to a substrate, such as wood and the like, which itself requires extended protection against microbial attack.

One well-known class of biocides are those containing a halopropargyl moiety, and especially an iodopropargyl moiety. Such compounds are widely disclosed in the patent literature including U.S. Pat. Nos. 3,660,499; 3,923,870; 4,259,350; 4,592,773; 4,616,004 and 4,639,460 to name a few. Included within this class of compounds are the halopropargyl carbamates which are known primarily for their fungicidal activity. 3-iodo-2-propynyl butyl carbamate, hereinafter also referred to as IPBC, is one of the best known and probably the most widely used of the halopropargyl carbamate fungicides. IPBC is a highly active broad spectrum fungicide. In addition to its fungicidal activity, IPBC also has been associated with algaecidal activity. In this regard, Great Britain Patent 2,138,292 and U.S. Pat. Nos. 4,915,909 and 5,082,722 contain such disclosures.

These compounds possess two reactive sites namely the carbon-carbon triple bond and the carbon-halogen, especially a carbon-iodine, bond. Depending on the pH of the system, nucleophiles, organic and inorganic acids and bases used in various applications can attack the halo(iodo) propargyl group, with gradual loss of the biocidal activity over time. Another kind of halo(iodo)propargyl instability is encountered in the dry film of coating compositions. The main cause of this decomposition mechanism is the exposure of the coating to shorter wavelengths of the electromagnetic spectrum of sunlight, namely ultraviolet radiation. This general phenomenon has been studied and documented by Gabriele et al., (U.S. Pat. No. 4,552,885). One approach taken by Gabriele et al to protect various biocides is to incorporate a combination of a piperidine compound and a UV absorber into the coating composition. Unfortunately, this approach has not heretofore been practical with the halo(iodo)propargyl compounds because the piperidine adjuvant used in conjunction with the UV absorbers destabilizes the halopropargyl compounds in the coating composition in aqueous formulations.

It is one object of the present invention, therefore, to provide a composition and method for stabilizing such halopropargyl, and especially iodopropargyl compounds, and most especially 3-iodo-2-propynyl butylcarbamate (IPBC), known in commerce as Troysan Polyphase®, not only in an ultimately dry film but also in aqueous compositions such as a latex paint. In this regard, it is especially an object of the invention to provide a stability-enhancing inclusion complex of a halopropargyl compound and especially IPBC.

Most of the compounds belonging to the class of halopropargyl compounds, and especially the iodopropargyls such as IPBC, also have a limited water solubility i.e., 50–300 ppm and therefore, such compounds are often times difficult to incorporate in systems which have water as a predominant ingredient.

It is therefore another object of the present invention to provide a water soluble inclusion complex of a halopropargyl compound, especially 3-iodo-2-propynyl butylcarbamate (IPBC).

BRIEF DESCRIPTION OF THE INVENTION

These and other objects are provided by the present invention which is based on a discovery that stability enhancing inclusion complexes, and especially water-soluble inclusion complexes, of such halopropargyl compounds, and especially IPBC, can be prepared using cyclodextrins and especially modified cyclodextrins.

DETAILED DESCRIPTION OF THE INVENTION

Cyclodextrins (CD) are a group of cyclic, homologous oligosaccharides that are obtained from the degradation of starch by the action of the enzyme cyclodextrin transglycosylase, such as produced by the bacterium *Bacillus macerans*. Cyclodextrins were first isolated by Filliers in 1891 as a digest of *Bacillus amylobacter* on potato starch, but the foundations of cyclodextrin chemistry were laid down by Schardinger in the period 1903–1911 and much of the older literature refers to cyclodextrins as Schardinger's dextrins. Until 1970, only small amounts of cyclodextrins could be produced in the laboratory and high production costs typically prevented their industrial use. In recent years, however, improvements in cyclodextrin production and purification have been made and the cyclodextrins have become much cheaper and commercially available. This has made industrial application of cyclodextrins possible.

Figure 1:
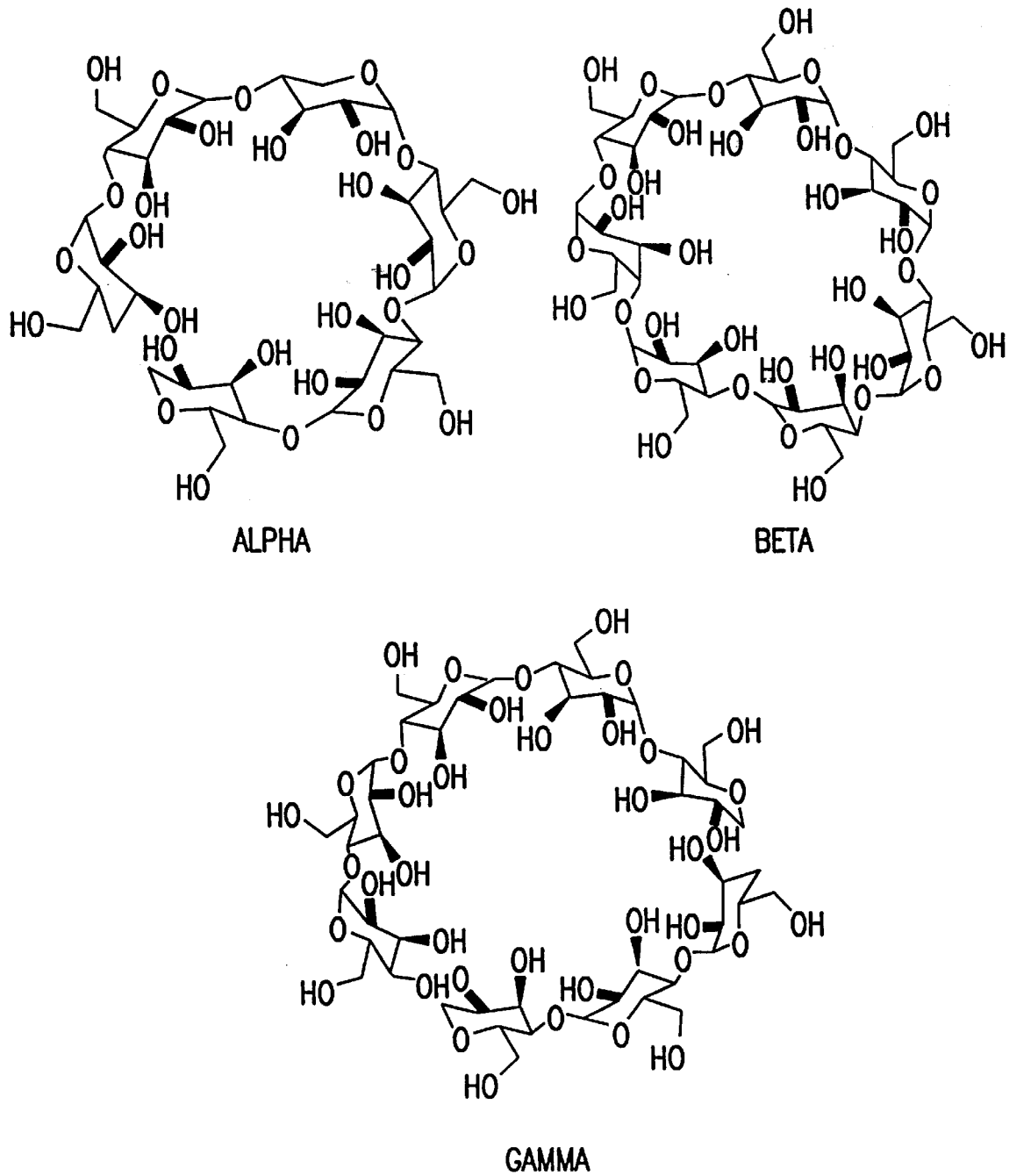
FIG. 1 schematically illustrates the basic structure of alpha (α), beta (β) and gamma (γ) cyclodextrins, such as before modifications to increase their water solubility.

Cyclodextrins are non-reducing dextrins which have a ring or donut shaped structure wherein glucopyranose units are joined to one another by α-1,4-glucoside linkages. Generally, α-cyclodextrin, β-cyclodextrin and γ-cyclodextrin, which consist of 6, 7, and 8 glucopyranose units, respectively, are well known. The structure of these compounds is schematically illustrated in FIG. 1. From the top view, the individual glucose units can be seen. The electron dense glycosidic oxygen atoms and the hydrogen atoms are oriented toward, and line the inner cavity of the three-dimensional structure. The hydrogen and glycosidic oxygen atoms lining the cavity give the cyclodextrin cavity a hydrophobic characteristic and an ability to interact with organic molecules or guest molecules to form inclusion complexes. It also is possible for some organic molecules and some inorganic salts to interact with the hydroxyl groups of the cyclodextrins.

It is believed that as a consequence of the cyclic arrangement and the conformation of the glucopyranose units, there is limited free rotation about the glycosidic bonds. The oligosaccharide ring thus forms a torus, as a truncated cone, with primary hydroxyl groups of each glucose residue lying on a narrow end of the torus, and with the secondary glucopyranose hydroxyl groups located on the wide end to provide a hydrophilic outer surface. The cavity is lined by hydrogen atoms from $C^3$ and $C^5$ along with the glucosidic oxygen atoms, and as noted above results in a relatively lipophilic (hydrophilic) cavity. Because their outer surface is hydrophilic, the cyclodextrins are soluble to various extents in water.

The parent cyclodextrin molecule, and useful derivatives, can be represented by the following unit formula (the ring carbons show conventional numbering) in which the vacant bonds represent the balance of the cyclic molecule (e.g., n=6–8):

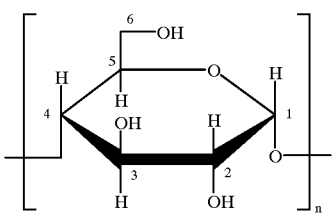

Each cyclodextrin molecule thus can potentially accommodate various kinds of compounds in the interior cavity of its ring structure to form an inclusion complex. As a result of the two separate polar regions and the changes in solvent structure that occur upon complexation, cyclodextrins have the ability to form complexes with a variety of organic and inorganic molecules. The formation of cyclodextrin inclusion complexes with a molecule is referred to as the host-guest phenomenon. Cyclodextrins have found wide use in medicines, agricultural chemicals, cosmetics and foods.

For a comprehensive review of cyclodextrins see *Cyclodextrins and Their Industrial Uses*, editor Dominique Duchene, Editions Santé, Paris, 1987. For a more recent overview, see J. Szejdi: Cyclodextrins in drug formulations: Part 1, *Pharm. Techn. Int.* 3(2), 15–22 (1991); and J. Szejtli: Cyclodextrins in drug formulations: Part II, *Pharm. Techn. Int.* 3(3), 16–24 (1991). A thorough discussion of inclusion complexes also can be found in R. J. Clarke, J. H. Coates and S. F. Lincoln, "Inclusion Complex of the Cyclomalto-Oligosaccharides (Cylodextrins)," *Advances in Carbohydrate Chemistry and Biochemistry*, vol. 46, pp. 205–249 (1989).

α-, β-, and γ-cyclodextrins have different physical properties from one another. The molecular weights, cavity dimensions and water solubility (at 25° C., g/100 ml. $H_2O$) of α-, β-, γ-cyclodextrin are provided below in Table 1.

TABLE 1

Physical Properties of Cyclodextrins

| Number of D-glucosyl residues | Name | Molecular weight | Solubility in water (g/100 ml.) | Cavity width (Å) |
|---|---|---|---|---|
| 6 | α-cyclodextrin | 972 | 14.5 | 5–6 |
| 7 | β-cyclodextrin | 1135 | 1.85 | 7–8 |
| 8 | γ-cyclodextrin | 1297 | 23.2 | 9–10 |

Published methods exist for the production of cyclodextrin transglycosylase as well as making and isolating the cyclodextrins themselves. Cyclodextrins generally are prepared by enzymatically modifying starch using an enzyme such as cyclodextrin glucosyltransferase. As is well-known, cyclodextrins are produced from starch of any selected plant variety such as corn, potato, waxy maize and the like, which may be modified or unmodified starch derived from cereal or tuber origin, and the amylose or amylopectin fractions thereof. The starch in aqueous slurry at a selected concentration up to about 35% by weight solids is usually liquefied as by gelatinization or treatment with a liquefying enzyme such as bacterial alpha-amylase enzyme and then subject to treatment with the transglycosylase enzyme to form the cyclodextrins.

Importantly, in the context of the present invention, the water solubility of the cyclodextrins may be increased by a variety of modifications. In this regard, it is known that the water solubility of β-cyclodextrin can be increased without necessarily interfering with its capacity to form inclusion complexes. For example, the outer hydroxyl groups can be reacted with ethylene oxide, propylene oxide, alkylhalides and the like to render the cyclodextrin, and the inclusion complexes made with the modified molecules water soluble. In a similar manner, the outer hydroxyl groups can be reacted with alkylene carbonates and preferably ethylene carbonate to form hydroxyethyl ethers on the ring structure. It is also known to produce cyclodextrin derivatives functionalized with $(C_{2-6}\text{alkylene})-SO_3-$ groups. Such derivatives also exhibit high aqueous solubility. The aqueous solubility exhibited by such derivatives is due to solvation of the sulfonic acid moieties. Other avenues of modification are recognized by those skilled in the art. The parent cyclodextrins and their modified versions are commercially available.

Preferably, the cyclodextrin derivatives are hydroxyalkylated α-, β-, γ-cyclodextrins typically having a degree of substitution of 1 to 5. The hydroxyalkyl substituents preferably contain 1–4 carbon atoms and up to 2 hydroxy groups. Particularly preferred cyclodextrin inclusion compounds according to the present invention are formed with modified cyclodextrins such as hydroxypropyl-α, hydroxypropyl-β or hydroxypropyl-γ. Hydroxypropyl-β-cyclodextrin and its preparation by propylene oxide addition to β-cyclodextrin, and hydroxyethyl-β-cyclodextrin and its preparation by ethylene oxide addition to β-cyclodextrin, were described over 20 years ago.

The present invention capitalizes on these characteristics of such cyclodextrins and especially such modified cyclodextrins to enable the preparation of inclusion complexes containing a halopropargyl compound as the guest. One discovery of the present invention is that such inclusion complexes provide protection for the halopropargyl compound guest, surprisingly improving its ability to the adverse effects of nucleophiles, varying pH and UV radiation. Especially useful are water soluble compositions containing a water soluble inclusion complex of a halopropargyl compound, preferably a halopropargyl carbamate and especially 3-iodopropargyl butylcarbamate. Thus, one aspect of the invention constitutes a water soluble composition containing an inclusion complex of a biocidal active halopropargyl compound and a water-soluble cyclodextrin.

A halopropargyl compound for use in the present invention can be identified by the following generic structure:

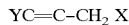

wherein Y is a halogen, preferably iodine and X can be (1) oxygen which is part of an organic functional group; (2) nitrogen which is part of an organic functional group; (3) sulfur which is part of an organic functional group; or (4) carbon which is part of an organic functional group.

The functional group of which oxygen is a part is preferably an ether, an ester, a carbamate group or heterocyclic compound. The functional group of which nitrogen is a part is preferably an amine, an amide, a urea, a nitrile, a carbamate group, or a heterocyclic compound. The functional group of which sulfur is a part is preferably a thiol, a thione, a sulfone, a sulfoxide group, or a heterocyclic compound. The organic functional group of which carbon is a part is preferably an ester, a carbamate, an alkyl group, or a heterocyclic compound.

Examples of compounds which may be used as the halopropargyl compound of this invention are especially the fungicidally active iodopropargyl derivatives. In this regard, please see U.S. Pat. Nos. 3,923,870, 4,259,350, 4,592,773, 4,616,004, 4,719,227, and 4,945,109, the disclosures of which are herein incorporated by reference. These iodopropargyl derivatives include compounds derived from propargyl or iodopropargyl alcohols such as the esters, ethers, acetals, carbamates and carbonates and the iodopropargyl derivatives of pyrimidines, thiazolinones, tetrazoles, triazinones, sulfamides, benzothiazoles, ammonium salts, carboxamides, hydroxamates, and ureas. Preferred among these compounds is the halopropargyl carbamate, 3-iodo-2-propynyl butyl carbamate APBC). This compound is included within the broadly useful class of compounds having the generic formula:

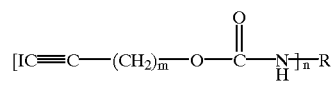

wherein R is selected from the group consisting of hydrogen, substituted and unsubstituted alkyl groups having from 1 to 20 carbon atoms, aryl, alkylaryl, and aralkyl groups having from 6 to 20 carbon atoms, and substituted and unsubstituted cycloalkyl and cycloalkenyl groups of 3 to 10 carbon atoms, and m and n are independently integers from 1 to 3, i.e., m and n are not necessarily the same.

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclopropargyl, cyclohexyl, aryls, alkaryls and aralkyls such as phenyl, benzyl, tolyl, cumyl, halogenated alkyls and aryls, such as chlorobutyl and chlorophenyl, and alkoxy aryls such as ethoxyphenyl and the like.

Especially preferred are such iodopropargyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

The inclusion complexes of the present invention are prepared by any method known in the art for the preparation of cyclodextrin inclusion complexes. In this regard, one may refer to U.S. Pat. No. 5,472,954 which describes the use of certain polymers in forming inclusion complexes. For example, to prepare a halopropargyl inclusion complex, a cyclodextrin or a modified cyclodextrin derivative is dissolved in water or in an organic solvent miscible with water. The solution then is mixed with the desired halopropargyl compound, which can be added in a solid form or dissolved in a solvent miscible with water. The mixture then is heated e.g., to a temperature of about 65°–75° C. and the desired inclusion complex is recovered by concentrating the mixture under reduced pressure, including lyophilization, or leaving the mixture to be cooled. It also is possible to heat only the cyclodextrin solution before addition of the halopropargyl compound. By varying the mixing ratio of any organic solvent with water one can accommodate the solubilities of the various starting materials or products.

The complex may be isolated by any suitable technique for example lyophilization, evaporation of the solvent, precipitation, low temperature crystallization, or spray-drying. Cyclodextrin inclusion complexes may also be produced by physically grinding or kneading the cyclodextrin and the guest molecule with or without a small amount of solvent. The ratio of cyclodextrin or a modified cyclodextrin derivative to halopropargyl compound used to prepare the inclusion complexes of the invention may be any convenient ratio but conveniently the cyclodextrin is used in a molar excess.

The benefits derived from the invention may be obtained by having the molar ratio of cyclodextrin to halopropargyl compound in the range of 10:1 to 1:10 preferably 1:1 to 5:1 for example 3:1. More usually, the cyclodextrins are employed in at least molar ratios of about 1:1 to about 2:1 to the halopropargyl compound. The use of highly concentrated cyclodextrin solutions is advantageous. Mixtures of various cyclodextrins can also be employed.

The amount of the halopropargyl compound in compositions containing an inclusion complex of the present invention, and particularly a water soluble inclusion complex of the present invention, can vary widely and an optimum amount generally is affected by the intended application and other components of a particular formulation. Generally, compositions, including both concentrated preparations and fully formulated products are likely to contain from 0.1 to 50 weight percent, more usually 1 to 40 weight percent and most often 1 to 25 weight percent of the active halopropargyl biocide. In any event, fully formulated compositions generally contain anywhere from about 0.001 to about 20 percent by weight of such halopropargyl compound. Usually, such compositions contain from 0.01 to 10 percent by weight of such compounds. Such compositions, protected against microbial attack by the inclusion of a halopropargyl carbamate, can be prepared from more concentrated compositions of the halopropargyl active ingredients by appropriate formulation or dilution. Oftentimes, the optimum useful range is about 0.1% to 1.0% of halopropargyl carbamate in a final formulation.

Upon the use of such formulations in end use systems, it is possible to protect surfaces as well as other substrates for extended periods of time against microbial growth, for example, from both algae and fungi. Suitable composition ranges for the two components are illustrated in Table 2. The compositions are reported as a weight percent based only on these two components.

TABLE 2

| Composition Range | Biocide Active Agent | Modified Cyclodextrin |
|---|---|---|
| 1 | 1–40 | 99–60 |
| 2 | 1–25 | 99–75 |

As noted above, compositions of the present invention, and particularly water soluble compositions of the invention, contain at least one biocidally active halopropargyl compound and especially a 3-iodopropargyl compound as described above, and at least one cyclodextrin or modified cyclodextrin, and preferably a water soluble cyclodextrin to form the inclusion complex and especially a water-soluble inclusion complex. As recognized by those skilled in the art, water solubility is a matter of degree. In the context of the present invention, an inclusion complex is considered water soluble if it has a degree of water solubility (measured under a convenient, though uniform, set of conditions, e.g., 25° C.) greater than the water solubility of the virgin guest halopropargyl compound, and preferably 10 times greater than the water solubility of the guest halopropargyl compound.

As noted above, the preparation and isolation of the cyclodextrin inclusion complex of the present invention is carried out by means of known techniques such as e.g., by mixing the cyclodextrin and the halopropargyl compound in the presence of a solvent followed by evaporation of the solvent at elevated temperature in vacuo, by crystallization, by lyophilzation or by precipitation upon addition of an organic solvent.

Water-soluble iodopropargyl carbamate inclusion complexes of the present invention prepared with a modified cyclodextrin of the present invention find particular application in metal working fluids, sap stain applications, textiles, soaps, adhesives, shampoos, cosmetics, creams, lotions, paper pulp, leather tanning, cooling water and many other applications where organic materials in an aqueous phase are present under conditions which allow the growth of undesired microorganisms. An extensive list of potential industries and applications for the present invention can be found in U.S. Pat. No. 5,209,930 which is herein incorporated by reference.

The following examples are presented to illustrate and explain the invention. Unless otherwise indicated, all references to parts and percentages are based on weight.

EXAMPLE 1

The modified cyclodextrin used for this example was a hydroxypropyl alpha cyclodextrin available commercially from American Maize-Products Company as Cavitron HPACD.

A 30% (wt/wt) solution of hydroxypropyl alpha cyclodextrin (HPACD) was prepared by dissolving 55 grams (dry basis) of Cavitron HPACD in 128.3 grams of water. The solution was heated to 70° C., and about 13 grams of Troysan Polyphase® P-100 (IPBC) all at once to this hot solution. The heat source was removed and the solution was allowed to cool to room temperature on its own. Insoluble, uncomplexed Troysan Polyphase® P-100 was filtered off and the residual filtrate was freeze dried to isolate the modified cyclodextrin inclusion complex of IPBC. The IPBC content in the complex was found to be about 15.2% using UV absorbance measurements.

The water solubility of the inclusion complex itself was found to be approximately 40%, i.e., about 40 parts of the complex dissolved in 100 parts of water, which translates to about 6% IPBC solubility in water. The formation of the inclusion complex in the disclosed composition thus increases the IPBC solubility in water by a factor of 250–300.

EXAMPLE 2

Four grams of IPBC were added to 96 g of water and stirred for ½ hour. The resulting slurry was filtered off and the filter cake was dried and weighed. Approximately 98% of the IPBC was recovered in the filter cake establishing the expected limited solubility of IPBC in water. Approximately 27 g of the lyophilized inclusion complex prepared in Example 1 was added to 73 g water and the mixture was stirred for ½ hour. The resulting clear solution had no solid materials left over. Use of the inclusion complex in this manner thus affords approximately 4% solution of IPBC in water, which is a solubility enhancement of approximately 250–300 times.

EXAMPLE 3

A 25% (wt/wt) solution of Cavitron Alpha cyclodextrin (ACD) was prepared by dissolving 160 grams (dry basis) of ACD in 480.0 grams of water. The solution was heated to 70° C., and 46.27 grams of Troysan PolyphaseR P-100 (IPBC) was added all at once to this hot solution. The heat source was removed and the solution was allowed to cool gradually to room temperature on its own. A precipitate formed and the resultant precipitate was collected by vacuum filtration, dried for 3 hours at 100–105° C., and milled using a Waring blender.

Half of the dried complexation product was then slurried in approximately 300 ml of acetone, and filtered to recover the washed complex. The filter cake was washed with additional acetone until the filtrate ran clear (about 200 ml of acetone). The washed complex was dried at 110° C. for one hour, and was again milled using a Waring blender. The IPBC content in the complex was found to be 11.8% by UV absorbance measurements.

EXAMPLE 4

The inclusion complexes of the invention find particular utility as an ingredient in lattices such as acrylic, vinyl acetate acrylic, polyvinyl acetate, styrene butadiene and silicone. Applications are also possible in paint, leather- and wood treatment fluids, metal-working fluids and plastic materials and many other applications where water and/or organic materials are present under conditions which allow the growth of undesired microorganisms. This example illustrates the surprising stability provided by such inclusion complexes relative to virgin IPBC.

The inclusion complex of Example 1, along with a positive control (Troysan Polyphase® P20T), were incorporated in a white styrenated acrylic house paint. The formulation of the white styrenated acrylic house paint is reported below in Table 3.

TABLE 3

Formulation of Styrenated House Paint

Formulation for Sytrenated Acrylic House Paint

| Raw Materials | Supplier | % (by weight) |
| --- | --- | --- |
| Water | | 9.30 |
| Start the Mixer and Add Slowly | | |
| Tamol 850 (30%) | Rohm & Haas | 0.20 |
| Triton CF-10 | Union Carbide | 0.50 |
| KTPP | FMC | 0.50 |
| NH$_4$OH (7.0%) | | 0.20 |
| Collacral P:Water (1:1) | BASF | 3.00 |
| Mix for 10 minutes and then add | | |
| Mineral Spirits | | 1.20 |
| Texanol | Eastman Chemicals | 0.80 |
| TiO$_2$ | Kerr-McGee | 15.00 |
| Camel White (CaCO$_3$) | Genstar | 26.00 |
| Nytal 300 | R.T. Vanderbilt | 6.40 |
| Disperse until smooth and then add | | |
| Nopco 8035 | Hüls AG | 0.30 |
| Acronal 296D | BASF | 36.60 |
| Add water to adjust viscosity | | |
| | | 100.00 |

The inclusion complex of Example 1 and Troysan Polyphase® P20T (20% IPBC) were incorporated in the above paint so that the active level of IPBC in the paint in both cases was 0.3% IPBC by weight. The paint samples along with a negative control (no biocide) were heat aged at 45° C. Draw-downs for these paints were made on Lanetta charts (initially having a unncoated portion and a portion with a clear film coating) to cover the entire chart and the charts were exposed to a UV light source (340 nm fluorescent bulb, Q Panel Company) for 48 hours. The paint films were examined thereafter for their yellowing characteristics relative to the negative control by measuring the yellowing index. The results are presented in Table 4.

TABLE 4

Protection Against Photochemical Degradation of IPBC.
Yellowing Index = Δb

| Paint sample with | Coated | Uncoated |
| --- | --- | --- |
| Troysan Polyphase ® P20T | 3.3 | 2.0 |
| Example 1 | 1.5 | 1.0 |

For these purposes Δb > 1.7 is considered a failure

Figure 2:
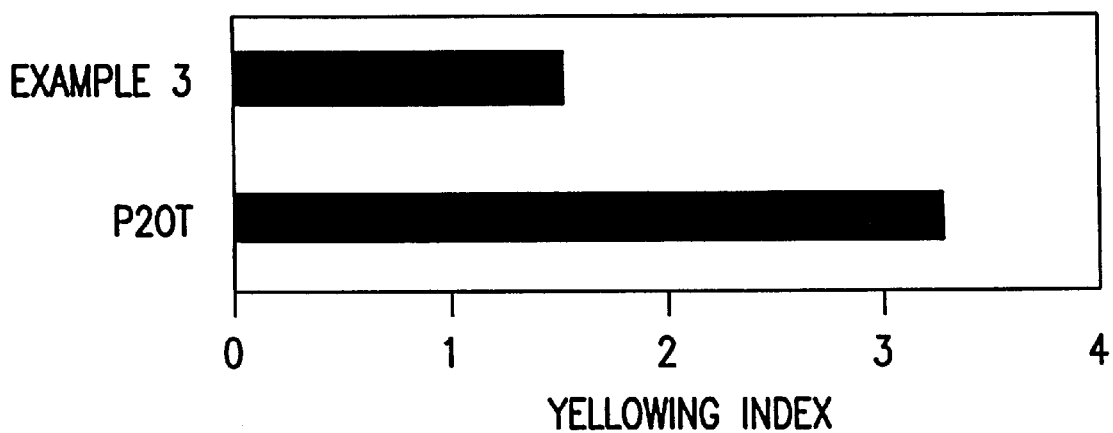
FIG. 2 graphically presents the stability enhancing effect provided by the inclusion complexes of the present invention.

The above results are shown graphically in FIG. 2. These results demonstrate that forming an inclusion complex of IPBC using a cyclodextrin protects the IPBC from degradation by UV light.

EXAMPLE 5

The melting point of pure IPBC is 66–67° C. and its decomposition occurs at about 150–155° C., leading to formation of highly colored by-products. The decomposition point of IPBC in the inclusion complex of Examples 1 and 3 was determined to be about 222–225° C. This demonstrates that IPBC inclusion complexes are thermally more stable than IPBC by itself.

While certain specific embodiments of the invention have been described with particularity herein, it will be recognized that various modifications thereof will occur to those skilled in the art and it is to be understood that such modifications and variations are to be included within the preview of this application and the spirit and scope of the appended claims.

I claim:

1. An inclusion complex of a haloproprynyl compound and an α cyclodextrin or a modified α cyclodextrin.

2. A biocidal composition containing an inclusion complex of a halopropynyl compound and an α cyclodextrin or a modified α cyclodextrin in water.

3. The composition of claim 2 wherein the halopropynyl compound is an iodopropynyl derivative selected from an iodopropynyl ester, an iodopropynyl ether, an iodopropynyl acetal, an iodopropynyl carbamate and an iodopropynyl carbonate.

4. The composition of claim 3 wherein the halopropynyl compound is an iodopropynyl carbamate of the formula:

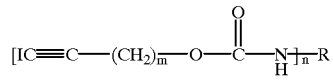

wherein R is selected from the group consisting of hydrogen, substituted and unsubstituted alkyl groups having from 1 to 20 carbon atoms, aryl, alkylaryl, and aralkyl groups having from 6 to 20 carbon atoms, and cycloalkyl and cycloalkenyl groups of 3 to 10 carbon atoms, and m and n are independent integers from 1 to 4.

5. The composition of claim 4 wherein the iodopropynyl carbamate is 3-iodo-2-propargylbutyl carbamate.

6. The composition of claim 5 wherein the modified α-cyclodextrin is hydroxypropyl-α cyclodextrin.

7. A water soluble inclusion complex of a halopropynyl compound and a modified α cyclodextrin.

8. A biocidal composition containing the water soluble inclusion complex of claim 7 and water.

9. The biocidal composition of claim 8 wherein the a halopropynyl compound is IPBC.

10. The composition of claim 9 wherein the modified cyclodextrin is hydroxypropyl α-cyclodextrin.

11. A water soluble inclusion complex of a halopropynyl compound and a modified α cyclodextrin, said modified α cyclodextrin having been modified to increase water solubility.

12. The inclusion complex of claim 11 wherein said modified α cyclodextrin is selected from a hydroxypropyl-α cyclodextrin and a hydroxyethyl-α cyclodextrin.

13. The inclusion complex of claim 11 wherein the halopropynyl compound is an iodopropynyl derivative selected from an iodopropynyl ester, an iodopropynyl ether, an iodopropynyl acetal, an iodopropynyl carbamate and an iodopropynyl carbonate.

14. The inclusion complex of claim 13 wherein the halopropynyl compound is an iodopropynyl carbamate of the formula:

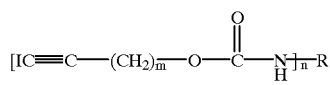

wherein R is selected from the group consisting of hydrogen, substituted and unsubstituted alkyl groups having from 1 to 20 carbon atoms, aryl, alkylaryl, and aralkyl groups having from 6 to 20 carbon atoms, and cycloalkyl and cycloalkenyl groups of 3 to 10 carbon atoms, and m and n are independent integers from 1 to 4.

15. The inclusion complex of claim 14 wherein the iodopropynyl carbamate is 3-iodo-2-propynyl butyl carbamate.

16. A biocidal composition containing the water soluble inclusion complex of claim 12 and water.

17. A biocidal composition containing the water soluble inclusion complex of claim 15 and water.

18. The composition of claim 6 wherein the modified α-cyclodextrin is a hydroxyalkylated α-cyclodextrin.

19. The composition of claim 18 wherein the modified α-cyclodextrin is hydroxypropyl α-cyclodextrin.

20. The water soluble inclusion complex of claim 7 wherein the modified cyclodextrin is a hydroxyalkylated α-cyclodextrin.

21. The water soluble inclusion complex of claim 20 wherein the modified cyclodextrin is hydroxypropyl α-cyclodextrin.

* * * * *